United States Patent
Pazenok et al.

(10) Patent No.: US 8,993,751 B2
(45) Date of Patent: Mar. 31, 2015

(54) PROCESS FOR PREPARING TETRAZOLE-SUBSTITUTED ANTHRANILIC ACID DIAMIDE DERIVATIVES BY REACTING BENZOXAZINONES WITH AMINES

(75) Inventors: Sergii Pazenok, Solingen (DE); Werner Lindner, Cologne (DE); Hartmut Scheffel, Wuppertal (DE)

(73) Assignee: Bayer Intellectual Property GmbH, Monheim am Rhein (DE)

( * ) Notice: Subject to any disclaimer, the term of this patent is extended or adjusted under 35 U.S.C. 154(b) by 0 days.

(21) Appl. No.: 14/240,224

(22) PCT Filed: Aug. 24, 2012

(86) PCT No.: PCT/EP2012/066477
§ 371 (c)(1),
(2), (4) Date: Feb. 21, 2014

(87) PCT Pub. No.: WO2013/030100
PCT Pub. Date: Mar. 7, 2013

(65) Prior Publication Data
US 2014/0194623 A1 Jul. 10, 2014

Related U.S. Application Data

(60) Provisional application No. 61/527,645, filed on Aug. 26, 2011.

(30) Foreign Application Priority Data

Aug. 26, 2011 (EP) .................................. 11179028

(51) Int. Cl.
C07D 413/14 (2006.01)
C07D 401/14 (2006.01)
C07D 405/14 (2006.01)

(52) U.S. Cl.
CPC ............ *C07D 413/14* (2013.01); *C07D 401/14* (2013.01); *C07D 405/14* (2013.01)
USPC .......................................... 544/92; 546/275.4

(58) Field of Classification Search
None
See application file for complete search history.

(56) References Cited

U.S. PATENT DOCUMENTS

| 8,324,390 B2 | 12/2012 | Fischer et al. |
| 2010/0029478 A1 | 2/2010 | Alig et al. |
| 2010/0256195 A1 | 10/2010 | Fischer et al. |

FOREIGN PATENT DOCUMENTS

| WO | 2004020445 A2 | 3/2004 |
| WO | 2006068669 A1 | 6/2006 |
| WO | 2007144100 A1 | 12/2007 |
| WO | 2010069502 A2 | 6/2010 |

OTHER PUBLICATIONS

International Search Report corresponding to PCT/EP2012/066477 mailed Feb. 11, 2013.
Norris, William P., "5-Trifluoromethyltetazole and Its Derivatives", J. Org. Chem, vol. 27, Issue 9, pp. 3248-3251, (1962).
Brown et al., "5-Perfluoroalkyletazoles. I. Ring-Opening Reactions", J. Org. Chem, vol. 32, Issue 6, pp. 1871-1873, (1967).
Curran et al., "Thermodynamics of Proton Ionization from Some Substituted, Unsaturated, Five-Membered Nitrogen Heterocycles (I)", J. Heterocycl. Chem., vol. 7, pp. 991-996, (1970).
Hansen et al.,"tris (2-Perfluorohexylethyl)tin azide: A New Reagent for Preparation of 5-Substituted Tetrazoles from Nitriles with Purification by Flourous/Organic Liquid-Liguid Extraction", Tetrahedron, vol. 55, Issue 29, pp. 8997-9006, (1999).
International Search Report from Corresponding PCT/EP2012/066477, received Feb. 11, 2013.

*Primary Examiner* — Timothy R Rozof
(74) *Attorney, Agent, or Firm* — Miles & Stockbridge PC

(57) ABSTRACT

The present invention relates to a process for preparing tetrazole-substituted anthranilic acid diamide derivatives of the formula (I)

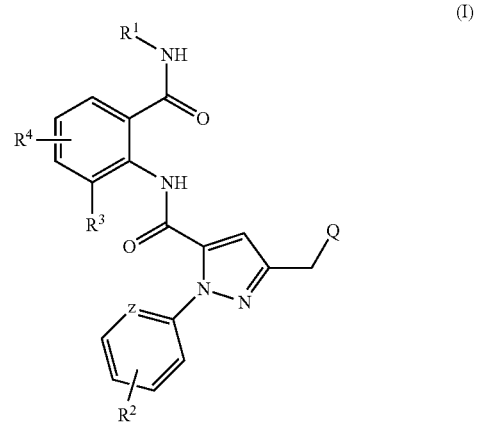

(I)

in which $R^1$, $R^2$, $R^3$, $R^4$, Q and Z have the meanings given in the description, by reacting benzoxazinones with amines.

9 Claims, No Drawings

PROCESS FOR PREPARING TETRAZOLE-SUBSTITUTED ANTHRANILIC ACID DIAMIDE DERIVATIVES BY REACTING BENZOXAZINONES WITH AMINES

CROSS REFERENCE TO RELATED APPLICATIONS

This application is a §371 National Stage Application of PCT/EP2012/066477, filed Aug .24, 2012, which claims priority from U.S. Provisional Patent Application No. 61/527,645, filed on Aug. 26, 2011, and to European Application No. 11179028.3, filed Aug. 26, 2011.

BACKGROUND OF THE INVENTION

1. Field of the Invention

The present invention relates to a process for preparing tetrazole-substituted anthranilic acid diamide derivatives of the formula (I)

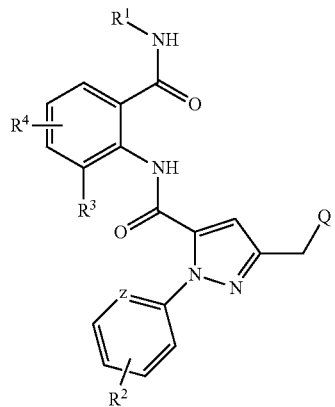

(I)

by reacting benzoxazinones with amines.

2. Description of Related Art

It has already been described in the literature that tetrazole-substituted anthranilic acid diamide derivatives can be prepared by reacting tetrazole-substituted N-aryl- and N-hetaryl-substituted pyrazole acids with anthranilamides (cf. WO2010/069502). It is also possible to obtain tetrazole-substituted anthranilic acid diamide derivatives by reacting tetrazole-substituted benzoxazinones with amines (WO 2010/069502). The reaction of benzoxazinones with amines proceeds selectively up to a conversion of 90-95%, but at the end of the reaction the tetrazole-substituted anthranilic acid diamide of the formula (I) reacts under basic conditions to form 4-oxo-3,4-dihydroquinazolines of the formula (X). This has a detrimental effect on the purity of the product and the efficiency of the process.

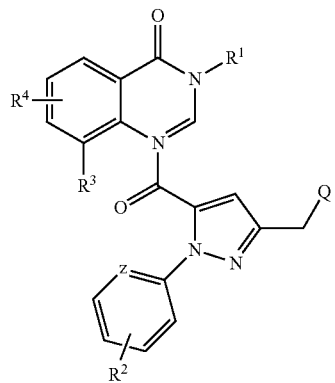

(X)

SUMMARY

Accordingly, it is an object of the present invention to provide novel economical processes for preparing tetrazole-substituted anthranilic acid diamide derivatives of the formula (I) in higher purity.

The object was achieved in accordance with the present invention by a process for preparing anthranilic acid diamide derivatives of the general formula (I)

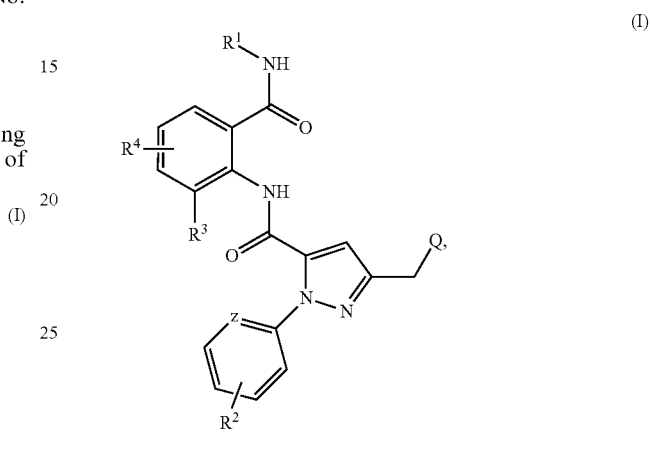

(I)

in which $R^1$, $R^3$ independently of one another represent hydrogen, or represent $C_1$-$C_6$-alkyl, $C_1$-$C_6$-alkoxy, $C_2$-$C_6$-alkenyl, $C_2$-$C_6$-alkynyl or $C_3$-$C_6$-cycloalkyl which are each optionally mono- or polysubstituted by identical or different halogen or nitro substituents, preferably represent ($C_1$-$C_5$)-alkyl, particularly preferably represent methyl, ethyl or tert-butyl, very particularly preferably represent methyl, $R^2$ represents $C_1$-$C_6$-alkyl, $C_3$-$C_6$-cycloalkyl, $C_1$-$C_6$-haloalkyl, $C_1$-$C_6$-halocycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$-alkoxy, $C_1$-$C_4$-haloalkoxy, alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, halogen, cyano, nitro, alkylamino, dialkylamino, cycloalkylamino or $C_3$-$C_6$-trialkylsilyl, preferably represents halogen or $C_1$-$C_6$-alkyl, particularly preferably represents fluorine or chlorine, very particularly represents chlorine, $R^4$ represents hydrogen, halogen, cyano, nitro, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_1$-$C_4$-alkoxy, $C_1$-$C_4$-haloalkoxy, $SF_5$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, haloalkylsulphonyl, $C_1$-$C_4$-alkylamino, di-($C_1$-$C_4$-alkyl) amino, $C_3$-$C_6$-cycloalkylamino, ($C_1$-$C_4$-alkoxy)imino, ($C_1$-$C_4$-alkyl)($C_1$-$C_4$-alkoxy)imino, ($C_1$-$C_4$-haloalkyl) ($C_1$-$C_4$-cyano, nitro, alkoxy)imino or $C_3$-$C_6$-trialkylsilyl, preferably represents hydrogen, chlorine or cyano, particularly preferably represents chlorine or cyano, very particularly preferably represents cyano, Q represents a tetrazole ring which is monosubstituted by $R^5$, preferably represents a tetrazole ring which is monosubstituted by $R^5$ and selected from the group consisting of

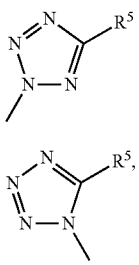

Q-1

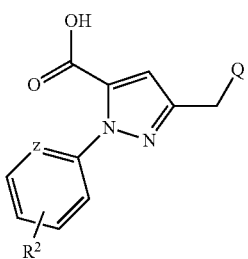

Q-2, particularly preferably represents Q-1, also particularly preferably represents Q-2, $R^5$ represents $C_1$-$C_5$-alkyl which may be mono- to trisubstituted by halogen, preferably represents $C_1$-$C_3$-perfluoroalkyl, particularly preferably represents $CF_3$ or $C_2F_5$, very particularly preferably represents $CF_3$, Z represents CH or N, preferably represents N, the compounds of the general formula (I) furthermore include N-oxides and salts, characterized in that tetrazole-substituted pyrazole acids of the formula (II)

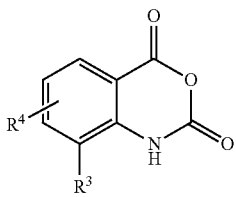

(II)

in which $R^2$, Q and Z have the meanings given above, are reacted with isatoic anhydrides of the formula (III)

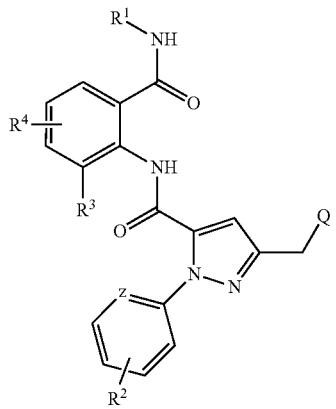

(III)

in which
$R^3$, $R^4$ have the meanings given above,
to give compounds of the formula (IV)

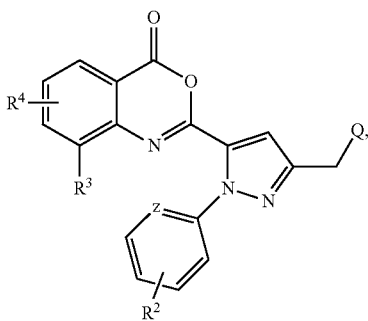

(IV)

in which $R^2$, $R^3$, $R^4$, Q and Z have the meanings given above, and these compounds of the general formula (IV) are reacted in the presence of an acid with amines of the general formula (V)

$R^1NH_2$ (V)

in which $R^1$ has the meanings given above,
to give anthranilic acid diamide derivatives of the formula (I), (I)

in which $R^1$, $R^2$, $R^3$, $R^4$, Q and Z have the meanings given above.

DETAILED DESCRIPTION OF A PREFERRED EMBODIMENT

The process according to the invention provides the compounds of the formula (I) in a purity of >93%, preferably 94%-98%, particularly preferably 95% to 97%, where the isomer ratio of the two possible regioisomers remains constant at from 90:10 to 96:4 (main isomer A, where Q represents Q-1: minor isomer B, where Q represents Q-2).

Main isomer A

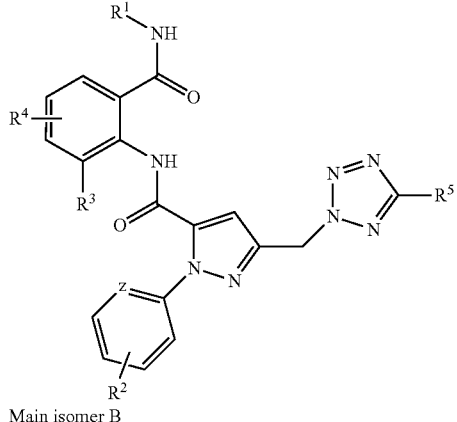

(A)

Main isomer B

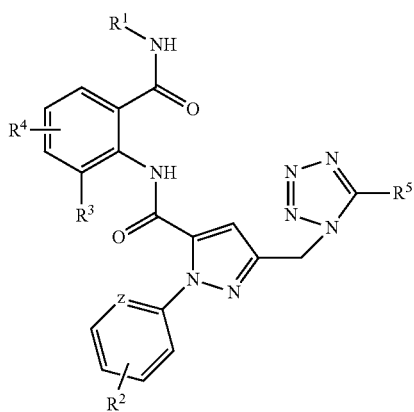

The process according to the invention can be illustrated by Scheme (I) below:

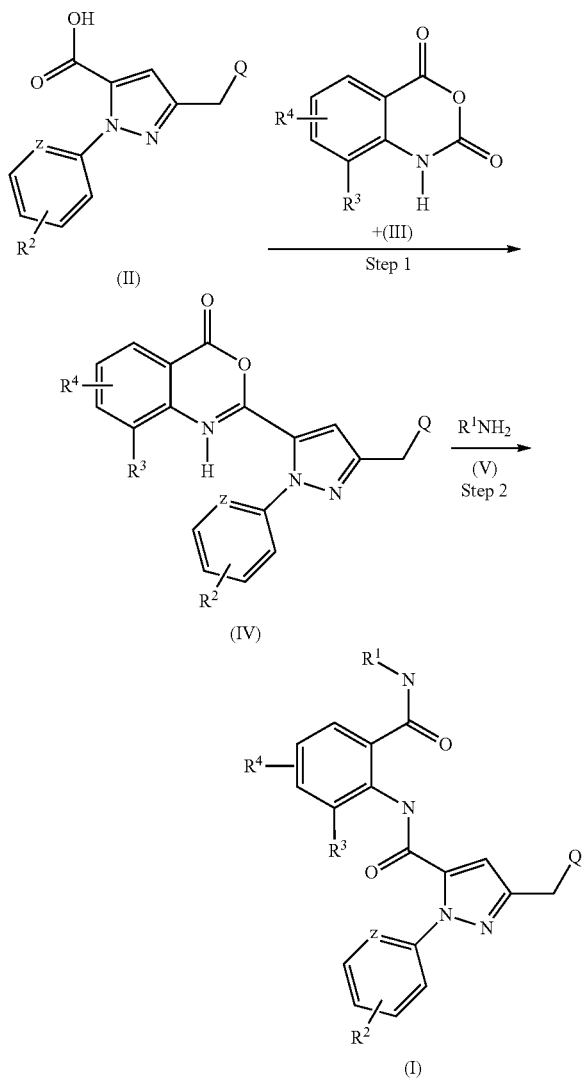

where R¹, R², R³, R⁴, Q and Z have the general meanings indicated above.

General Definitions

In the context of the present invention, the term halogens (X) comprises, unless defined otherwise, elements selected from the group consisting of fluorine, chlorine, bromine and iodine, with fluorine, chlorine and bromine being preferred and fluorine and chlorine being particularly preferred. Substituted groups may be mono- or polysubstituted, where in the case of polysubstitution the substituents can be identical or different.

Alkyl groups substituted by one or more halogen atoms (—X) (=haloalkyl groups) are, for example, selected from trifluoromethyl ($CF_3$), difluoromethyl ($CHF_2$), $CCl_3$, $CFCl_2$, $CF_3CH_2$, $ClCH_2$, $CF_3CCl_2$.

In the context of the present invention, alkyl groups are, unless defined otherwise, straight-chain or branched hydrocarbon groups.

The definitions alkyl and $C_1$-$C_{12}$-alkyl include, for example, the meanings methyl, ethyl, n-, isopropyl, n-, iso-, sec- and t-butyl, n-pentyl, n-hexyl, 1,3-dimethylbutyl, 3,3-dimethylbutyl, n-heptyl, n-nonyl, n-decyl, n-undecyl, n-dodecyl.

In the context of the present invention, cycloalkyl groups are, unless defined otherwise, cyclic saturated hydrocarbon groups.

In the context of the present invention, aryl radicals are, unless defined otherwise, aromatic hydrocarbon radicals which may have one, two or more heteroatoms selected from O, N, P and S and may optionally be substituted by further groups.

In the context of the present invention, arylalkyl groups and arylalkoxy groups are, unless defined otherwise, alkyl and alkoxy groups, respectively, which are substituted by aryl groups and may have an alkylene chain. Specifically, the definition arylalkyl includes, for example, the meanings benzyl- and phenylethyl; the definition arylalkoxy includes, for example, the meaning benzyloxy.

In the context of the present invention, alkylaryl groups (alkaryl groups) and alkylaryloxy groups are, unless defined otherwise, aryl groups and aryloxy groups, respectively, which are substituted by alkyl groups and may have a $C_{1-8}$-alkylene chain and may have one or more heteroatoms selected from O, N, P and S in the aryl skeleton or aryloxy skeleton.

If appropriate, the compounds according to the invention may be present as mixtures of various possible isomeric forms, in particular of stereoisomers, such as, for example, E and Z, threo and erythro, and also optical isomers, and, if appropriate, also of tautomers. What are disclosed are both the E and the Z isomers, and also the threo and erythro, and the optical isomers, any mixtures of these isomers and the possible tautomeric forms.

Step 1

2,4-Dioxo-1,4-dihydro-2H-3,1-benzoxazines (isatoic anhydrides) of the formula (III) are known (WO 2006/068669).

The compounds of the formula (IV) (benzoxazinones) are obtained by reacting tetrazole-substituted pyrazole acids of the formula (II) with anthranilic acid derivatives of the formula (III).

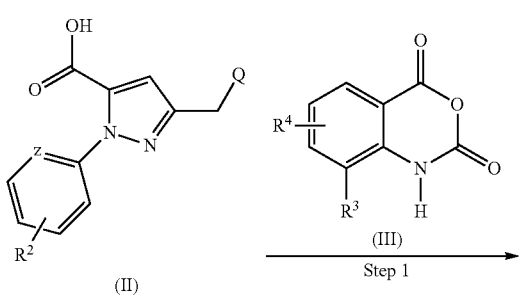

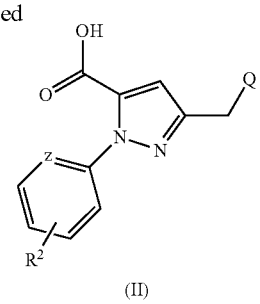

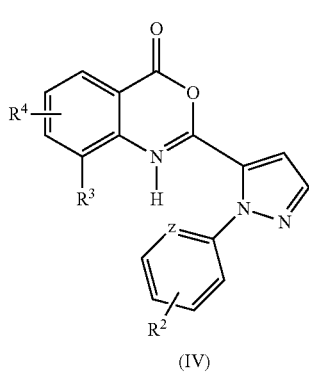

Pyrazole acids of the formula (II) are known (cf. WO2007/144100). Pyrazole acids of the formula (II) can be prepared, for example, from halomethylpyrazole esters of the formula (VI) and perfluoroalkyltetrazoles of the formula (VII) in two steps a and b (cf. Scheme (II) and Preparation Examples). Here, the compounds of the formula (VIII) formed are converted by basic hydrolysis (step b) into the pyrazole acids of the formula (II).

Scheme (II)

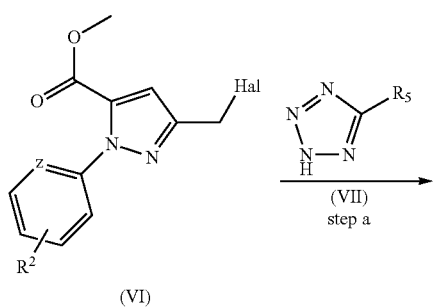

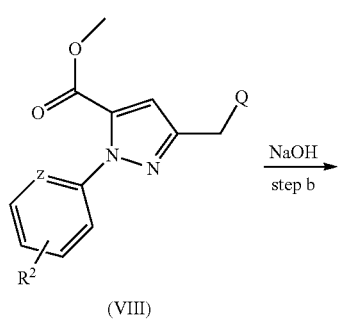

Halomethylpyrazole esters of the formula (VI) are likewise known and can be prepared as described in WO 2011/7073101. Perfluoroalkyltetrazoles of the formula (VII) are known; some of them are even commercially available, or they can be obtained by known processes (cf., for example, WO2004/020445; William P. Norris, *J. Org. Chem.*, 1962, 27 (9), 3248-3251; Henry C. Brown, Robert J. Kassal, *J. Org. Chem.*, 1967, 32 (6), 1871-1873; Dennis P Curran, Sabine Hadida, Sun-Young Kim, *Tetrahedron*, 1999, 55 (29), 8997-9006; L. D. Hansen, E. J. Baca, P. Scheiner, *Journal of Heterocyclic Chemistry*, 1970, 7, 991-996, JACS V. 27, p. 3248).

Step 1

As a basic principle, Step 1 is carried out in the presence of a base. Suitable bases are, for example, sodium hydroxide, potassium carbonate, sodium carbonate, caesium carbonate, sodium methoxide. Preference is given to organic bases such as trialkylamines, pyridines, alkylpyridines, phosphazenes and 1,8-diazabicyclo[5.4.0]undecene (DBU). Particular preference is given to pyridines, alkylpyridines such as β-picoline, 2,6-dimethylpyridine, 2-methyl-5-ethylpyridine, 2,3-dimethylpyridine. When carrying out Process Step 1 according to the invention, preferably from 1.5 mol to 4 mol, particularly preferably from 1.5 to 3 equivalents, of the base are employed per mole of the pyrazole of the formula (II). Step 1 is carried out in the presence of a condensing agent. Suitable for this purpose are all agents customary for such coupling reactions. Examples which may be mentioned are acid halide formers such as phosgene, phosphorus tribromide, phosphorus trichloride, phosphorus pentachloride, phosphorus oxychloride or thionyl chloride; anhydride formers such as ethyl chloroformate, methyl chloroformate, isopropyl chloroformate, isobutyl chloroformate or methanesulphonyl chloride, p-toluenesulphonyl chloride; carbodiimides such as N,N'-dicyclohexylcarbodiimide (DCC) or other customary condensing agents such as phosphorus pentoxide, polyphosphoric acid, 1,1'-carbonyldiimidazole, 2-ethoxy-N-ethoxycarbonyl-1,2-dihydroquinoline (EEDQ), triphenylphosphine/carbon tetrachloride, bromotripyrrolidinophosphonium hexafluorophosphate, bis(2-oxo-3-oxazolidinyl)phosphinic chloride or benzotriazol-1-yloxy-tris(dimethylamino)phosphonium hexafluorophosphate. Polymer-supported reagents such as, for example, polymer-bound cyclohexylcarbodiimide may also be used. Particularly suitable are methanesulphonyl chloride (mesyl chloride) and phosgene. When carrying out Process Step 1 according to the according to the invention, preferably from 1 mol to 3 mol, particularly preferably from 1.5 to 2.5 mol, of the condensing agent are employed per mole of the pyrazole of the formula (II).

The process step according to the invention is preferably carried out within a temperature range of from 0° C. to +80° C., particularly preferably at temperatures of from 10° C. to +50° C.

When carrying out the process step according to the invention, an equimolar amount of the compound of the formula (III) is employed per mole of the pyrazole acid of the formula (II).

The Process Step (1) according to the invention is generally carried out under atmospheric pressure. However, it is alternatively also possible to operate under reduced pressure or under elevated pressure.

The reaction time is not critical and may be chosen in a range between one and a plurality of hours, depending on the batch size, on the substituent $R^5$ and on the temperature.

Suitable solvents are, for example, aliphatic, alicyclic or aromatic hydrocarbons such as, for example, petroleum ether, n-hexane, n-heptane, cyclohexane, methylcyclohexane, benzene, toluene, xylene or decalin, and halogenated hydrocarbons such as, for example, chlorobenzene, dichlorobenzene, dichloromethane, chloroform, carbon tetrachloride, dichloroethane or trichloroethane, ethers such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles such as acetonitrile, propionitrile, n- or isobutyronitrile or benzonitrile; amides such as N,N-dimethylformamide, N,N-dimethylacetamide, N-methylformanilide, N-methylpyrrolidone or hexamethylphosphoric triamide; sulphoxides such as dimethyl sulphoxide or sulphones such as sulpholane, alcohols such as methanol, ethanol, isopropanol. Particular preference is given to using acetone, acetonitrile, toluene, methyl tert-butyl ether, THF. Particularly suitable are acetonitrile, THF, DMF and NMP.

Step 2

The compounds of the formula (IV) formed in Step 1 are converted into anthranilic acid diamide derivatives of the formula (I):

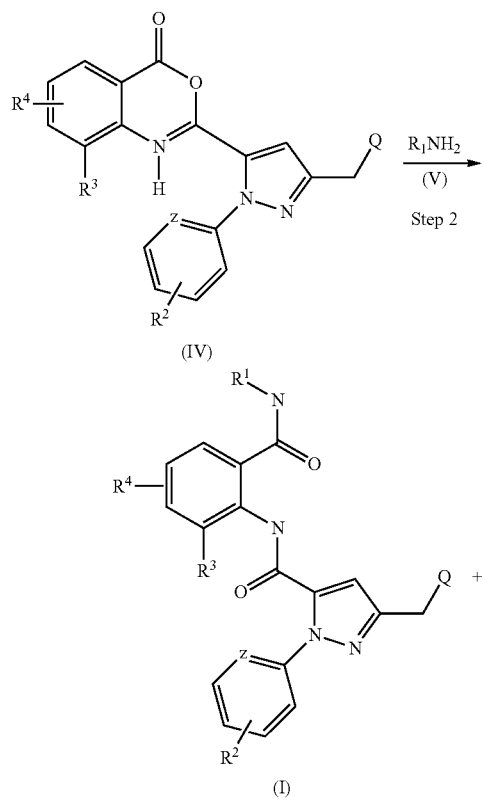

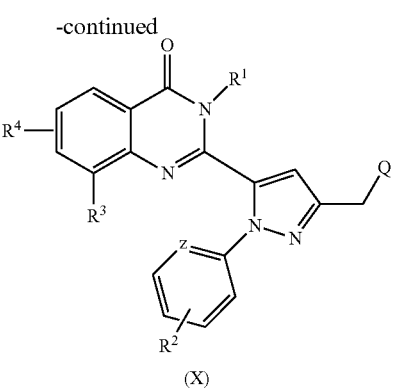

Surprisingly, it has now been found that, in the presence of an acid, the compounds of the formula (IV) react selectively and under very mild conditions to give anthranilic acid diamide derivatives of the formula (I), the formation of minor components, in particular the formation of 4-oxo-3,4-dihydroquinazoline-6-carbonitrile of the formula (X), being substantially suppressed. The purity of the product is significantly improved thereby.

Very mild conditions are to be understood, for example, as meaning the following conditions; however, this is not limiting:

The reaction is generally carried out under atmospheric pressure. However, it is alternatively also possible to operate under elevated pressure (for example reaction with MeNH$_2$ in an autoclave).

Depending on the batch size and temperature, the reaction time can be chosen in a range between 1 hour and a plurality of hours.

The Process Step (2) according to the invention is preferably carried out within a temperature range of from 0° C. to +100° C., particularly preferably at temperatures of from 10° C. to +80° C., very particularly preferably at 10-60° C.

The reaction step is preferably carried out in a solvent. Suitable solvents are, for example, selected from the group consisting of water, alcohols such as methanol, ethanol, isopropanol or butanol, aliphatic and aromatic hydrocarbons such as, for example, n-hexane, benzene or toluene which may be substituted by fluorine and chlorine atoms, such as methylene chloride, dichloroethane, chlorobenzene or dichlorobenzene; ethers such as, for example, diethyl ether, diphenyl ether, methyl tert-butyl ether, isopropyl ethyl ether, dioxane, diglyme, dimethyl glycol, dimethoxyethane (DME) or THF; nitriles such as methyl nitrile, butyl nitrile or phenyl nitrile; amides such as dimethylformamide (DMF) or N-methylpyrrolidone (NMP), or mixtures of such solvents, with water, acetonitrile, dichloromethane and alcohols (ethanol) being particularly suitable. Particular preference is given to THF, acetonitrile, alcohols.

The amines of the formula (V) can be used neat or as a solution in water, THF, acetonitrile or alcohols or in another solvent.

What are used are the compounds of the formula (V) where $R^1$ preferably represents ($C_1$-$C_6$)-alkyl.

Suitable acids are organic and inorganic acids such as HCOOH, CH$_3$COOH, CF$_3$COOH, p-TSA, CH$_3$SO$_3$H, HCl, H$_2$SO$_4$, HF, HBr, HBF$_4$. Particularly preferred are CH$_3$COOH and CH$_3$SO$_3$H. For carrying out the Process Step (2) according to the invention, for 1 mol of the benzoxazinone of the formula (IV), preferably 0.001 mol to 1.5 mol, more preferably 0.01 mol to 1 mol, particularly preferably 0.01 to 0.5 mol, very particularly preferably 0.01 mol to 0.3 mol, especially preferably 0.1 mol to 0.3 mol of the acid is used.

The Process Step (2) according to the invention is generally carried out under atmospheric pressure. However, it is alternatively also possible to operate under reduced pressure or under elevated pressure in an autoclave.

Depending on the batch size and the temperature, the reaction time can be chosen in a range between 1 hour and a plurality of hours.

It is also possible to carry out the Steps 1 and 2 with intermediate isolation of benzoxazinones.

PREPARATION EXAMPLES

The following Preparation Examples illustrate the invention without limiting it.

Example 1

Isomer mixture of methyl 1-(3-chloropyridin-2-yl)-3-{[5-(trifluoromethyl)-2H-tetrazol-2-yl]methyl}-1H-pyrazole-5-carboxylate (main isomer) and methyl 1-(3-chloropyridin-2-yl)-3-{[5-(trifluoromethyl)-1H-tetrazol-1-yl]methyl}-1H-pyrazole-5-carboxylate (minor component).

2.86 g (0.01 mol) of methyl 3-(chloromethyl)-1-(3-chloropyridin-2-yl)-1H-pyrazole-5-carboxylate and 1.6 g (0.01 mol) of sodium 5-(trifluoromethyl)tetrazol-2-ide and 0.15 g of KI in 50 ml of acetone were heated at 56° C. for 12 hours. The salts were filtered off and the acetone was removed under reduced pressure. This gave 3.59 g of the product as a 9:1 mixture of the two isomers.
Analytical characterization
Main Isomer
$^1$H NMR (CD$_3$CN) δ: 8.52 (1H, d); 7.95 (1H, d), 7.45 (1H, dd); 7.10 (1H, s); 6.05 (2H, s); 3.75 (3H, s) ppm.
$^{19}$F NMR −64.05 ppm.
Minor Component
$^{19}$F NMR −61.46 ppm.
$^1$H NMR (CD$_3$CN) δ: 8.50 (1H, d); 7.90 (1H, d), 7.45 (1H, dd); 6.95 (1H, s); 5.80 (2H, s); 3.70 (3H, s) ppm.

Example 2

Isomer mixture of 1-(3-chloropyridin-2-yl)-3-{[5-(trifluoromethyl)-2H-tetrazol-2-yl]methyl}-1H-pyrazole-5-carboxylic acid (main isomer) and 1-(3-chloropyridin-2-yl)-3-[5-(trifluoromethyl)-1H-tetrazol-1-yl]-1H-pyrazole-5-carboxylic acid (minor component).

3.59 g of the mixture from Example 1 were dissolved in 40 ml of methanol, and 2 g of NaOH were added as a 10% strength solution in water. The mixture was stirred at RT for 3 hours.

10% strength HCl was added to adjust the pH of the solution to 3, and the product was extracted with methyl tert-butyl ether. After removal of the solvent, 3 g of the product having a purity of 99% are obtained.
Analytical Characterization Main Isomer 92%
$^1$H NMR (CD$_3$CN) δ: 13.5 (bs), 8.52 (1H, d); 8.2 (1H, d), 7.6 (1H, dd); 7.2 (1H, s); 6.25 (2H, s) ppm.
$^{19}$F NMR −64.25 ppm.

Example 3

Isomer mixture of methyl 2-[1-(3-chloropyridin-2-yl)-3-{[5-(trifluoromethyl)-2H-tetrazol-2-yl]methyl}-1H-pyrazol-5-yl]-8-methyl-4-oxo-4H-3,1-benzoxazine-6-carbonitrile and 2-[1-(3-chloropyridin-2-yl)-3-{[5-(trifluoromethyl)-1H-tetrazol-1-yl]methyl}-1H-pyrazol-5-yl]-8-methyl-4-oxo-4H-3,1-benzoxazine-6-carbonitrile 18.83 g (50 mmol) of 1-(3-chloropyridin-2-yl)-3-{[5-(trifluoromethyl)-2H-tetrazol-2-yl]methyl}-1H-pyrazole-5-carboxylic acid were initially charged in 60 ml of acetonitrile and the mixture was cooled to 0° C.

16.3 g of b-picoline and 8.16 g of methanesulphonyl chloride were added in succession, and the mixture was stirred at 0° C. for 1 hour. 10.1 g of 8-methyl-2,4-dioxo-1,4-dihydro-2H-3,1-benzoxazine-6-carbonitrile were then added, and the reaction mixture was stirred at 50° C. for 10 hours and cooled to 10° C. 50 ml of water were added to the suspension and the precipitate was filtered off and washed with water. This gave 23.9 g (yield 93%) of benzoxazinones in the isomer ratio 91:9.
$^1$H NMR (DMF d$_6$) main isomer δ: 8.71 dd), 8.41 (1H, d); 8.40 (1H, dd), 8.11 (1H, m); 7.84 (1H, dd), 7.68 (1H, s), 6.48 (2H, s), 1.83 (3H, s) ppm.

Example 4

Isomer mixture of 1-(3-chloropyridin-2-yl)-N-[4-cyano-2-methyl-6-(methylcarbamoyl)-phenyl]-3-{[5-(trifluoromethyl)-2H-tetrazol-2-yl]methyl}-1H-pyrazole-5-carboxamide (main isomer) and 1-(3-chloropyridin-2-yl)-N-[4-cyano-2-methyl-6-(methylcarbamoyl)phenyl]-3-[5-(trifluoromethyl)-1H-tetrazol-1-yl]-1H-pyrazole-5-carboxamide (minor component) in a ratio of 92:8.

51.3 g of the isomer mixture of 2-({[1-(3-chloropyridin-2-yl)-3-{[5-(trifluoromethyl)-2H-tetrazol-2-yl]methyl}-1H-pyrazol-5-yl]-8-methyl-4-oxo-4H-3,1-benzoxazine-6-carbonitrile from Example 3 were suspended in 200 ml of acetonitrile at 30° C. 1.5 ml of CH$_3$COOH were then added and subsequently 1.2 equivalents of methylamine (as a solution in THF) were added dropwise at 20° C. The mixture was stirred at 30° C. for 4 hours and diluted with 100 ml of water, and the suspension was stirred for 3 hours at 50° C. The precipitate was filtered off and dried. This gave 52 g (yield 93%) of the product as a white solid having an isomer ratio of 92:8 and a purity of 97% (w/w). The content of 2-[1-(3-chloropyridin-2-yl)-3-{[5-(trifluoromethyl)-2H-tetrazol-2-yl]-methyl}-1H-pyrazol-5-yl]-3,8-dimethyl-4-oxo-3,4-dihydroquinazoline-6-carbonitrile was 0.1%.
Analytical Characterization

| Main isomer | | | | | | |
|---|---|---|---|---|---|---|
| H/C | δH/ppm | Mult. | rel. No. H | δC/ppm | Mult. | rel. No. C |
| 1 | — | — | — | 118.7 | Q | 1 |
| 2 | — | — | — | 156.1 | Q | 1 |
| 3 | 6.34 | S | 2 | 51.3 | T | 1 |
| 4 | — | — | — | 145.6 | S | 1 |
| 5 | 7.40 | S | 1 | 108.5 | D | 1 |
| 6 | — | — | — | 138.8 | S | 1 |
| 7 | — | — | — | 156.3 | S | 1 |
| 8 | 10.55 | S | 1 | — | — | — |
| 9 | — | — | — | 137.6 | S | 1 |
| 10 | — | — | — | 138.7 | S | 1 |
| 11 | — | — | — | 166.2 | S | 1 |
| 12 | 8.38 | Q | 1 | — | — | — |
| 13 | 2.66 | D | 3 | 26.3 | Q | 1 |
| 14 | 7.75 | D | 1 | 129.7 | D | 1 |
| 15 | — | — | — | 109.4 | S | 1 |
| 16 | — | — | — | 118.3 | S | 1 |
| 17 | 7.87 | D | 1 | 135.2 | D | 1 |
| 18 | — | — | — | 138.0 | S | 1 |
| 19 | 2.20 | S | 3 | 18.0 | Q | 1 |
| 20 | — | — | — | 149.1 | S | 1 |
| 21 | — | — | — | 128.0 | S | 1 |

13

-continued

Main isomer

| H/C | δH/ppm | Mult. | rel. No. H | δC/ppm | Mult. | rel. No. C |
|---|---|---|---|---|---|---|
| 22 | 8.16 | DD | 1 | 139.4 | D | 1 |
| 23 | 7.60 | DD | 1 | 126.7 | D | 1 |
| 24 | 8.48 | DD | 1 | 147.3 | D | 1 |

Minor component

| H/C | δH/ppm | Mult. | rel. No. H | δC/ppm | Mult. | rel. No. C |
|---|---|---|---|---|---|---|
| 1 | — | — | — | 118.1 | Q | 1 |
| 2 | — | — | — | 145.9 | Q | 1 |
| 3 | 6.11 | S | 2 | 47.0 | T | 1 |
| 4 | — | — | — | 145.9 | S | 1 |
| 5 | 7.35 | S | 1 | 107.7 | D | 1 |
| 6 | — | — | — | 138.8 | S | 1 |
| 7 | — | — | — | 156.2 | S | 1 |
| 8 | 10.54 | S | 1 | — | — | — |
| 9 | — | — | — | 137.6 | S | 1 |
| 10 | — | — | — | 135.2 | S | 1 |
| 11 | — | — | — | 166.2 | S | 1 |
| 12 | 8.37 | Q | 1 | — | — | — |
| 13 | 2.66 | D | 3 | 26.3 | Q | 1 |
| 14 | 7.75 | D | 1 | 129.7 | D | 1 |
| 15 | — | — | — | 109.3 | S | 1 |
| 16 | — | — | — | 118.3 | S | 1 |
| 17 | 7.87 | D | 1 | 135.4 | D | 1 |
| 18 | — | — | — | 138.0 | S | 1 |
| 19 | 2.19 | S | 3 | 17.9 | Q | 1 |
| 20 | — | — | — | 149.1 | S | 1 |
| 21 | — | — | — | 128.1 | S | 1 |
| 22 | 8.14 | DD | 1 | 139.4 | D | 1 |
| 23 | 7.58 | DD | 1 | 126.7 | D | 1 |
| 24 | 8.47 | DD | 1 | 147.2 | D | 1 |

Example 5

The procedure of Example 4 was followed; however, 1 ml of HCl (37%) was used. This gave 51.2 g of the product having a purity of 96%. The proportion of 2-[1-(3-chloropyridin-2-yl)-3-{[5-(trifluoromethyl)-2H-tetrazol-2-yl]methyl}-1H-pyrazol-5-yl]-3,8-dimethyl-4-oxo-3,4-dihydroquinazoline-6-carbonitrile was 0.3%.

Example 6

The procedure of Example 5 was followed; however, no CH₃COOH was used. This gave 50 g of the product having a purity of 92%. The proportion of 2-[1-(3-chloropyridin-2-yl)-3-{[5-(trifluoro-methyl)-2H-tetrazol-2-yl]methyl}-1H-pyrazol-5-yl]-3,8-dimethyl-4-oxo-3,4-dihydroquinazoline-6-carbonitrile was 3%.

The invention claimed is:
1. Process for preparing a compound of formula (I)

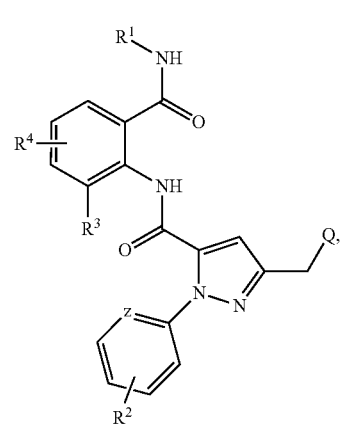

(I)

in which
R$^1$, R$^3$ independently of one another represent hydrogen, or represent C$_1$-C$_6$-alkyl, C$_1$-C$_6$-alkoxy, C$_2$-C$_6$-alkenyl, C$_2$-C$_6$-alkynyl or C$_3$-C$_6$-cycloalkyl which are each optionally mono- or polysubstituted by identical or different halogen or nitro substituents,
R$^2$ represents C$_1$-C$_6$-alkyl, C$_3$-C$_6$-cycloalkyl, C$_1$-C$_6$-haloalkyl, C$_1$-C$_6$-halocycloalkyl, C$_2$-C$_6$-alkenyl, C$_2$-C$_6$-haloalkenyl, C$_2$-C$_6$-alkynyl, C$_2$-C$_6$-haloalkynyl, C$_1$-C$_4$-alkoxy, C$_1$-C$_4$-haloalkoxy, C$_1$-C$_4$-alkylthio, C$_1$-C$_4$-alkylsulphinyl, C$_1$-C$_4$-alkylsulphonyl, C$_1$-C$_4$-haloalkylthio, C$_1$-C$_4$-haloalkylsulphinyl, C$_1$-C$_4$-haloalkylsulphonyl, halogen, cyano, nitro, alkylamino, dialkylamino, cycloalkylamino or C$_3$-C$_6$-trialkylsilyl,
R$^4$ represents hydrogen, halogen, cyano, nitro, C$_1$-C$_4$-alkyl, C$_1$-C$_4$-haloalkyl, C$_2$-C$_6$-alkenyl, C$_2$-C$_6$-haloalkenyl, C$_2$-C$_6$-alkynyl, C$_1$-C$_4$-alkoxy, C$_1$-C$_4$-haloalkoxy, SF$_5$, C$_1$-C$_4$-alkylthio, C$_1$-C$_4$-alkylsulphinyl, C$_1$-C$_4$-alkylsulphonyl, C$_1$-C$_4$-haloalkylthio, C$_1$-C$_4$-haloalkylsulphinyl, C$_1$-C$_4$-haloalkylsulphonyl, C$_1$-C$_4$-alkylamino, di-(C$_1$-C$_4$-alkyl)amino, C$_3$-C$_6$-cycloalkylamino, (C$_1$-C$_4$-alkoxy)imino, (C$_1$-C$_4$-alkyl)(C$_1$-C$_4$-alkoxy)imino, (C$_1$-C$_4$-haloalkyl)(C$_1$-C$_4$-cyano, nitro, alkoxy)imino or C$_3$-C$_6$-trialkylsilyl,
Q represents a tetrazole ring which is monosubstituted by R$^5$, optionally a tetrazole ring which is monosubstituted by R$^5$ and selected from the group consisting of

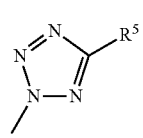

Q-1

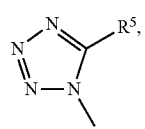

Q-2

R$^5$ represents C$_1$-C$_5$-alkyl which may be mono- to trisubstituted by halogen,
Z represents CH or N,
the compound of formula (I) furthermore may include an N-oxide and/or a salt thereof, wherein said process comprises reacting a tetrazole-substituted pyrazole acid of formula (II)

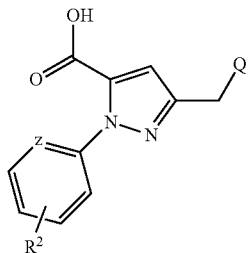 (II)

with an isatoic anhydride of formula (III)

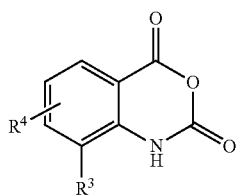 (III)

to give a compound of formula (IV)

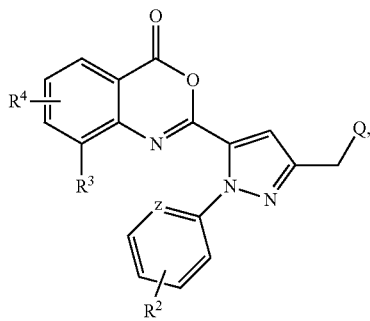 (IV)

and reacting said compound of formula (IV) in the presence of an acid with an amine of formula (V)

$R^1NH_2$ (V), to give a compound of formula (I) and/or an N-oxide and/or a salt thereof.

2. Process according to claim 1, wherein
$R^1$, $R^3$ independently of one another represent ($C_1$-$C_5$)-alkyl,
$R^2$ represents halogen or $C_1$-$C_6$-alkyl,
$R^4$ represents hydrogen, chlorine or cyano,
Q represents a tetrazole ring which is monosubstituted by $R^5$ and selected from the group consisting of

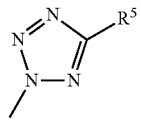 Q-1

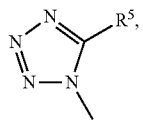 Q-2

$R^5$ represents ($C_1$-$C_3$)-perfluoroalkyl,
Z represents N.

3. Process according claim 1, wherein
$R^1$, $R^3$ independently of one another represent methyl, ethyl or tert-butyl,
$R^2$ represents fluorine or chlorine,
$R^4$ represents chlorine or cyano,
Q represents Q-1 or Q-2,
$R^5$ represents $CF_3$ or $C_2F_5$,
Z represents N.

4. Process according to claim 1, wherein $R^5$ represents $CF_3$.

5. Process according to claim 1, wherein $R^2$ represents chlorine,
$R^3$ represents methyl and $R^4$ represents cyano.

6. Process according to claim 1, wherein the ratio of compounds of the formula (I) in which Q represents Q-1 to compounds of the formula (I) in which Q represents Q-2 is from 90:10 to 96:4.

7. Process according to claim 1, wherein, when the compound of formula (IV) is reacted with the compound of formula (V), from 0.001 to 1.5 mol of an organic and/or inorganic acid is added per 1 mol of compound of formula (IV).

8. Process according to claim 1, wherein, when the compound of formula (IV) is reacted with the compound of formula (V), from 0.01 to 0.3 mol of $CF_3COOH$ is added per 1 mol of compound of formula (IV).

9. Process according to claim 1, wherein the compound of formula (IV) is reacted at a reaction temperature of from 0° C. to +100° C. with the compound of formula (V) to give an anthranilic acid diamide derivative of formula (I) and/or an N-oxide and/or a salt thereof.

* * * * *